US00PP12968P2

(12) United States Plant Patent
van Rijn

(10) Patent No.: US PP12,968 P2
(45) Date of Patent: Sep. 17, 2002

(54) ANTHURIUM PLANT NAMED 'MARTINE'

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 39 days.

(21) Appl. No.: 09/837,567

(22) Filed: Apr. 18, 2001

(51) Int. Cl.[7] ..... A01H 5/00

(52) U.S. Cl. ..... Plt./365

(58) Field of Search ..... Plt./365

(56) References Cited

PUBLICATIONS

UPOV–ROM GTITM Computer Database 2001/01, GTI JOUVE Retrieval Software, citation(s) for 'Martine' Feb. 6, 2001.*

* cited by examiner

*Primary Examiner*—Bruce R. Campell
*Assistant Examiner*—Annette H. Para
(74) *Attorney, Agent, or Firm*—C. A. Whealy

(57) ABSTRACT

A distinct cultivar of Anthurium plant named 'Martine', characterized by its upright and somewhat outwardly spreading plant habit; dark green leaves; white and pink bi-colored spathes with pink-colored spadices that are positioned upright and beyond the foliage on strong and erect scapes; and good inflorescence longevity.

2 Drawing Sheets

BACKGROUND OF THE INVENTION

The present invention relates to a new and distinct cultivar of Anthurium plant, botanically known as *Anthurium andreanum*, and hereinafter referred to by the name 'Martine'.

The new Anthurium is a product of a planned breeding program conducted by the Inventor in Schipluiden, The Netherlands. The objective of the program is to create and develop new freely flowering Anthurium cultivars with strong roots, dark green leaves, attractive spathe color, and good inflorescence longevity.

The new Anthurium originated from a cross by the Inventor in 1994 of the Inventor's proprietary *Anthurium andreanum* selection code number 93-0026 as the female, or seed, parent with the Inventor's proprietary *Anthurium andreanum* selection code number 90-0023 as the male, or pollen, parent. The cultivar Martine was discovered and selected by the Inventor as a plant within the progeny of the stated cross in a controlled environment in Schipluiden, The Netherlands in 1996.

Asexual propagation of the new cultivar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Martine. These characteristics in combination distinguish 'Martine' as a new and distinct cultivar:

1. Upright and somewhat outwardly spreading plant habit.
2. Durable dark green leaves.

3. White and pink bi-colored spathes with pink-colored spadices that are positioned upright and beyond the foliage on strong and erect scapes.
4. Freely flowering habit.
5. Good inflorescence longevity.

The new Anthurium can be compared to the female parent, the selection 93-0026. In side-by-side comparisons conducted in Schipluiden, The Netherlands, plants of the new Anthurium differ from plants of the selection 93-0026 in the following characteristics:

1. Plants of the new Anthurium have larger leaves than plants of the selection 93-0026.
2. Plants of the new Anthurium have more durable leaves than plants of the selection 93-0026.

The new Anthurium can be compared to the male parent, the selection 90-0023. In side-by-side comparisons conducted in Schipluiden, The Netherlands, plants of the new Anthurium differ from plants of the selection 90-0023 in the following characteristics:

1. Plants of the new Anthurium grow faster than plants of the selection 90-0023.
2. Plants of the new Anthurium are more freely flowering than plants of the selection 90-0023.

The new Anthurium can also be compared to the cultivar Cleopatra, disclosed in U.S. Plant Pat. No. 11,456. In side-by-side comparisons conducted in Schipluiden, The Netherlands, plants of the new Anthurium differ from plants of the cultivar Cleopatra in the following characteristics:

1. Plants of the new Anthurium have smaller, less rounded and lighter green leaves than plants of the cultivar Cleopatra.
2. Plants of the new Anthurium and the cultivar Cleopatra differ in spathe coloration.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph on the first sheet comprises a side perspective view of a typical potted plant of the cultivar Martine that was about one year old.

The photograph at the top of the second sheet comprises a close-up view of a typical inflorescence of 'Martine'.

The photograph at the bottom of the second sheet comprises a close-up view of a typical leaf of 'Martine'.

DETAILED BOTANICAL DESCRIPTION

In the following description, color references are made to The Royal Horticultural Society Colour Chart except where general terms of ordinary dictionary significance are used. The following observations and measurements describe 1-year old plants grown in 19-cm containers in Schipluiden, The Netherlands, in a glass greenhouse with an average day temperature of 25° C. and an average night temperature of 19° C.

Botanical classification: *Anthurium andreanum* cultivar Martine.

Parentage:

*Female parent.*—Inventor's proprietary *Anthurium andreanum* selection code number 93-0026, not patented.

*Male parent.*—Inventor's proprietary *Anthurium andreanum* selection code number 90-0023, not patented.

Propagation:

*Method.*—By tissue culture.

*Time to develop roots on a tissue-cultured cutting.*—About 70 or 84 days at 24° C. or 21° C., respectively.

*Root description.*—Strong fleshy roots.

Plant description:

*Plant shape.*—Upright and somewhat outwardly spreading, inverted triangle, symmetrical.

*Growth habit.*—Freely clumping, bushy and dense. Appropriate for 13 to 40-cm containers. Vigorous.

*Plant height.*—About 40 to 60 cm.

*Crop time.*—About 9 months are usually required from planting of young plants to finished plants in a 19-cm container.

*Foliage description.*—Quantity per plant: About 40. Length: About 10 to 27 cm. Width: About 6 to 17 cm. Shape: Cordate. Apex: Apiculate to cuspidate. Base: Auriculate; lobes not overlapping. Margin: Entire. Texture: Smooth, glabrous, leathery. Venation pattern: Pinnate. Color: Young leaves, upper surface: Between 137A and 146A. Young leaves, lower surface: 146A. Mature leaves, upper surface: 147A; venation, 144A. Mature leaves, lower surface: 146A; venation, 144A. Petiole: Length: About 10 to 35 cm. Color: 144A. Geniculum length: About 1 to 3 cm. Geniculum color: 144A.

Inflorescence description:

*Inflorescence arrangement.*—Spathes with spadices held beyond the foliage. Flowering structures arise from leaf axils. Freely and continuous flowering year-round; typically more than 20 inflorescences per plant.

*Inflorescence longevity.*—Inflorescences last about six weeks under winter conditions and about three months under summer conditions; persistent.

*Spathe.*—Length: About 8 to 12 cm. Width: About 8 to 11 cm. Shape: Cordate. Apex: Apiculate to mucronulate. Base: Auriculate; lobes not overlapping. Margin: Entire. Texture: Leathery, glabrous, some blistering. Color: When opening: Apex and center, 155C overlain with 62C; towards base, 144B; glossy. Opened, front and back surfaces: 155A; venation, 62A; towards base, 144B, glossy.

*Spadix.*—Length: About 5 to 8 cm. Diameter: About 8 mm. Shape: Columnar. Cross section: Rounded. Longitudinal axis: Erect. Color: Immature: 144C. Mature: Towards apex: 62D. Towards base: 58D.

*Flowers.*—Quantity per spadix: Numerous, about 200. Shape: Rounded. Diameter: About 1 mm, maximum.

*Reproductive organs.*—Androecium: Pollen color: 159D. Gynoecium: Stigma shape: Ovoid.

*Scape.*—Length: About 27 to 38 cm. Aspect: Strong and erect. Color: Immature, 146A, mature, 182B.

*Seed.*—Seed development on plants of the new Anthurium has not been observed.

Disease/pest resistance: Under commercial conditions, plants of the new Anthurium have not been observed to be resistant to pathogens or pests common to Anthurium.

It is claimed:

1. A new and distinct cultivar of Anthurium plant named 'Martine', as illustrated and described.

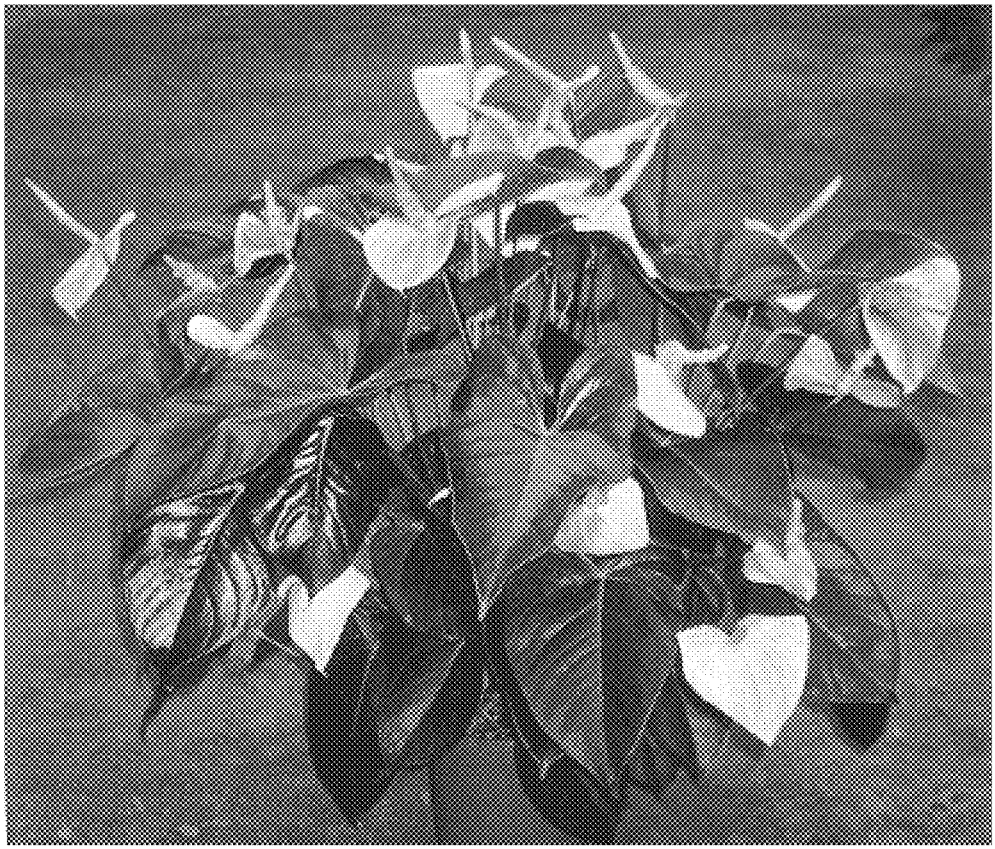

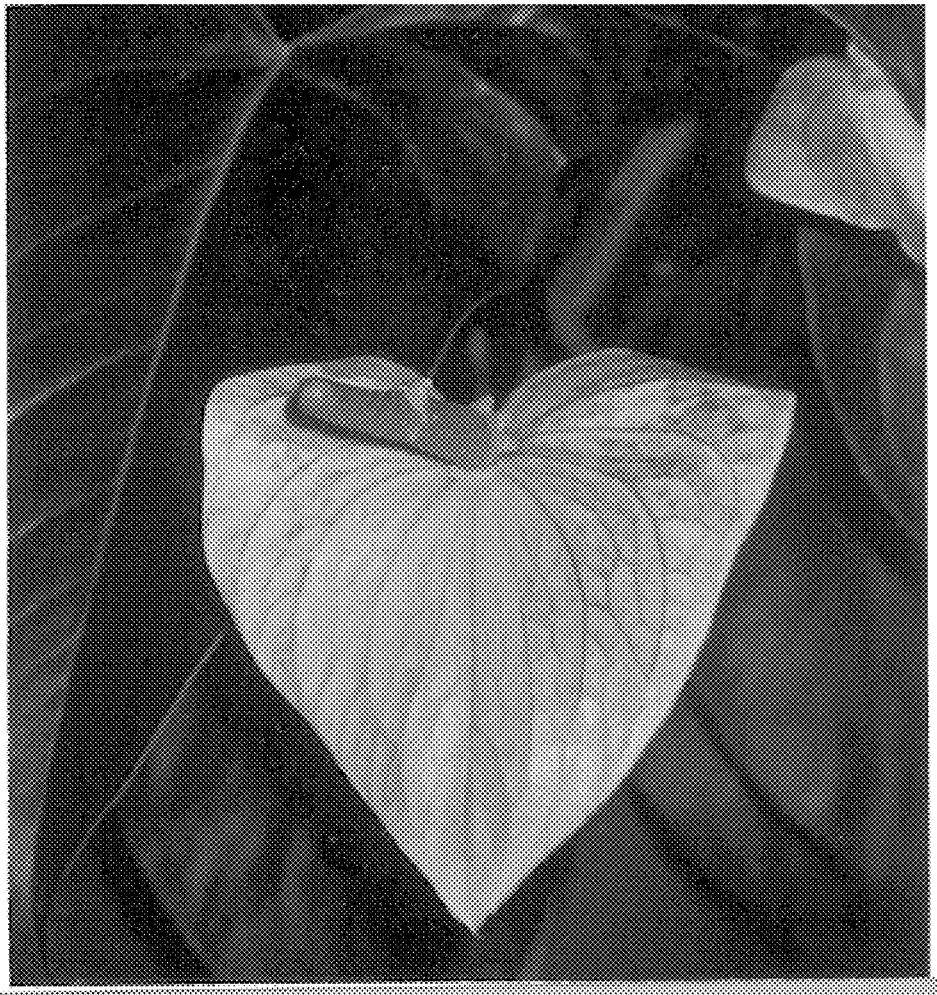
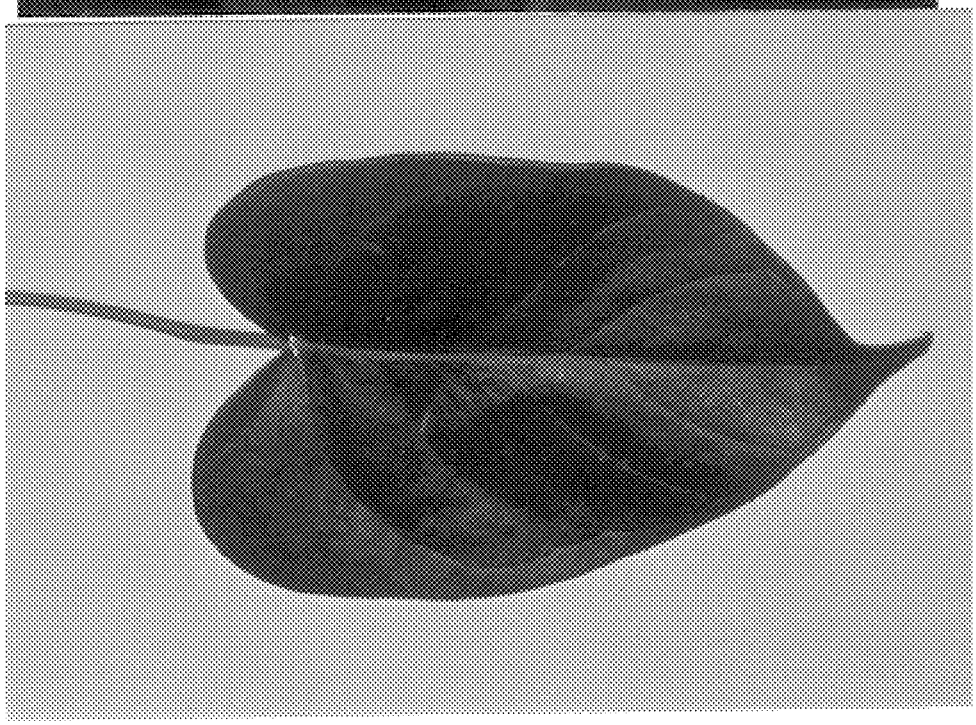

* * * * *